(12) United States Patent
Kane-Esrig (10) Patent No.: US 9,519,863 B2
(45) Date of Patent: Dec. 13, 2016

(54) METHOD AND APPARATUS FOR A PREDICTIVE TRACKING DEVICE

(71) Applicant: Alcatel Lucent, Paris (FR)

(72) Inventor: Yana Kane-Esrig, Madison, NJ (US)

(73) Assignee: Alcatel Lucent, Boulogne-Billancourt (FR)

( * ) Notice: Subject to any disclaimer, the term of this patent is extended or adjusted under 35 U.S.C. 154(b) by 107 days.

(21) Appl. No.: 14/272,868

(22) Filed: May 8, 2014

(65) Prior Publication Data

US 2014/0244555 A1 Aug. 28, 2014

Related U.S. Application Data

(63) Continuation of application No. 13/196,033, filed on Aug. 2, 2011, now Pat. No. 8,768,864.

(51) Int. Cl.
| | |
|---|---|
| *G06F 15/18* | (2006.01) |
| *G06N 5/04* | (2006.01) |
| *G06F 19/00* | (2011.01) |
| *A61B 5/16* | (2006.01) |
| *A61B 5/00* | (2006.01) |
| *G06N 99/00* | (2010.01) |
| *A61B 5/11* | (2006.01) |

(52) U.S. Cl.
CPC ............ *G06N 5/04* (2013.01); *A61B 5/165* (2013.01); *A61B 5/7275* (2013.01); *G06F 19/3437* (2013.01); *G06N 99/005* (2013.01); *A61B 5/1118* (2013.01)

(58) Field of Classification Search
CPC ..... A61B 5/165; A61B 5/7275; A61B 5/1118; G06F 19/3437; G06N 5/04; G06N 99/005

USPC ........................................................... 706/12
See application file for complete search history.

(56) References Cited

U.S. PATENT DOCUMENTS

| | | | |
|---|---|---|---|
| 4,142,067 A | 2/1979 | Williamson | |
| 6,544,200 B1 * | 4/2003 | Smith | A61B 5/1117 340/573.1 |
| 6,980,149 B1 * | 12/2005 | Meyer | H04L 67/38 340/4.4 |
| 7,616,110 B2 * | 11/2009 | Crump | A61B 5/02055 128/903 |
| 8,125,314 B2 * | 2/2012 | Fithian | G06Q 10/00 340/1.1 |
| 8,346,688 B2 * | 1/2013 | Carroll | G06F 19/3437 706/12 |

(Continued)

OTHER PUBLICATIONS

Learning Parameter-Advising Sets for Multiple Sequence Alignment D. DeBlasio; J. Kececioglu IEEE/ACM Transactions on Computational Biology and Bioinformatics Year: 2015, vol. PP, Issue: 99 pp. 1-1, DOI: 10.1109/TCBB.2015.2430323 IEEE Early Access Articles.*

(Continued)

*Primary Examiner* — Michael B Holmes
(74) *Attorney, Agent, or Firm* — Carl Biliscka (57) ABSTRACT

A predictive tracking method and apparatus utilizing objective and subjective data in order to predict user states is provided herein. For example, some such embodiments may allow a user to track their mood or health symptoms in relation to retrieved data regarding their environmental in order to reveal patterns that can help forecast and proactively manage mood or health symptoms.

30 Claims, 9 Drawing Sheets

(56) References Cited

U.S. PATENT DOCUMENTS

| | | | | |
|---|---|---|---|---|
| 8,378,811 | B2* | 2/2013 | Crump | A61B 5/02055 |
| | | | | 128/903 |
| 8,768,864 | B2* | 7/2014 | Kane-Esrig | G06F 19/3437 |
| | | | | 700/46 |
| 2002/0198991 | A1 | 12/2002 | Gopalakrishnan et al. | |
| 2006/0009702 | A1 | 1/2006 | Iwaki et al. | |
| 2009/0106040 | A1 | 4/2009 | Jones | |
| 2009/0131758 | A1* | 5/2009 | Heywood | A61B 5/0002 |
| | | | | 600/300 |
| 2011/0022369 | A1* | 1/2011 | Carroll | G06N 3/02 |
| | | | | 703/11 |
| 2011/0124996 | A1* | 5/2011 | Reinke | A61M 5/14248 |
| | | | | 600/365 |
| 2011/0178969 | A1 | 7/2011 | Falchuk et al. | |
| 2012/0221310 | A1* | 8/2012 | Sarrafzadeh | A61B 5/0205 |
| | | | | 703/11 |
| 2013/0036080 | A1* | 2/2013 | Kane-Esrig | G06F 19/3437 |
| | | | | 706/46 |
| 2013/0141460 | A1* | 6/2013 | Kane-Esrig | H04M 3/5116 |
| | | | | 345/633 |
| 2014/0074807 | A1* | 3/2014 | Kane-Esrig | G06F 8/71 |
| | | | | 707/695 |
| 2014/0244555 | A1* | 8/2014 | Kane-Esrig | G06F 19/3437 |
| | | | | 706/12 |

OTHER PUBLICATIONS

The On-line Electronic Commerce Forecast Based on Least Square Support Vector Machine M. Zhou; Q. Wang Information and Computing Science, 2009. ICIC '09. Second International Conference on Year: 2009, vol. 2 pp. 75-78, DOI: 10.1109/ICIC.2009.127 IEEE Conference Publications.*

Performance Weighted Deploying and Scheduling Strategy Research for Virtual Machine on Clouds G. Fen; M. Hua-Qing; Y. Jie Emerging Intelligent Data and Web Technologies (EIDWT), 2013 Fourth International Conference on Year: 2013 pp. 56-60, DOI: 10.1109/EIDWT.2013.14 IEEE Conference Publications.*

Mobile User Profile Acquisition through Network Observables and Explicit User Queries N. Bila; J. Cao; R. Dinoff; T. K. Ho; R. Hull; B. Kumar; P. Santos Mobile Data Management, 2008. MDM '08. 9th International Conference on Year: 2008 pp. 98-107, DOI: 10.1109/MDM.2008.34 IEEE Conference Publications.*

PCT International Search Report dated Jan. 13, 2015 (PCT/US2012/046176) 2 pages.

Guzman, et. al., "Mood-Worsening With High-Pollen-Counts and Seasonality: A Preliminary Report," NIH Public Access, Published in final edited form as: J Affect Disord. Aug. 2007; 101 (1-3): 269-274.

J. K. Darby, et al., "Speech and Voice Parameters of Depression: A Pilot Study." Department of Neurobiology, Stanford Univ. School of Medicine, Stanford, CA, USA; Institute for Advanced Study of Comm. Processes (IASCP), Univ. of Florida, Gainesville, Fla.; Louisiana Rehabilitation Institute, New Orleans, LA; Stanford Univ. School of Medicine, Stanford, CA, USA. Elsevier Science Publishing Co., Inc., New York, NY. 1984, pp. 75-85.

Renew—Stress on the Brain, © 2004—The Franklin Institute Online—All rights reserved. web article available online at http://www.fi.edu/learn/brain/stress.html.

Michael Trei, Wrist Worn Emotion Sensor is Like a Mood Ring for the 21st Century, Oct. 31, 2010. web article available online at http://dvice.com/archives/2010/10/wrist-worn-emot.php.

"Mobile Diary: Java Application from Ultima Square: Date Dec. 28, 2010." available online at http://handheld.softpedia.com/get/Word-Processing-Text-Tools/Journal/MobileDiary-68572.shtml.

Diary.com iPhone App: Date = 2010. available online at http://diary.com/mobile.

"FreshApp Diary: Frontier Code: current version is Jul. 21, 2011." available online at http://www.freshapps.com/diary/.

"iChemoDiary: by Mercy & Co. Inc.: Jan. 12, 2011." available online at http://itunes.apple.com/us/app/ichemodiary/id334253464?mt=8#.

"Momento Diary." available online at http://www.momentoapp.com.

"Android Dolphin Browser: Jul. 30, 2010.", available online at http://news.softpedia.com/news/Dolphin-Browser-HD-Brilliant-Browser-for-Android-149976.shtml.

Jaroslaw Cichosz and Krzysztof Slot, "Emotion Recognition in Speech Signal Using Emotion-Extracting Binary Decision Trees," Institute of Electronics, Technical University of Lodz, Wolczanska 211/215, 90-924 Lodz, Poland. Retrieved from the internet on Mar. 7, 2011. 8 pages.

"Momento Diary." Retrieved from the internet on Jul. 21, 2011. 4 pages. available online at http://www.momentoapp.com/.

"Google Gesture Search." Retrieved from the internet on Jul. 21, 2011. 1 page. available online at http://gesturesearch.googlelabs.com/.

\* cited by examiner

|  | ENV. DATUM | DATE/TIME | LOCATION |
|---|---|---|---|
| T1-R1 | POLLEN COUNT = 10 | 2011-02-24 | HOME |
|  | POLLEN COUNT = 15 | 2011-02-24 | OFFICE |
|  | ACTIVITY = EXERCISE | 2011-02-24 8:34 | GYM |
| T1-R3 | POLLEN COUNT = 70 | 2011-02-25 | HOME |
|  | POLLEN COUNT = 50 | 2011-02-25 | OFFICE |
|  | POLLEN COUNT = 150 | 2011-02-26 | HOME |
|  | POLLEN COUNT = 40 | 2011-02-26 | OFFICE |
|  | ACTIVITY = EXERCISE | 2011-02-26 8:39 | GYM |
|  | POLLEN COUNT = 100 | 2011-02-27 | HOME |
|  | ACTIVITY = EXERCISE | 2011-02-27 10:00 | GYM |

T1-C2 above DATE/TIME column; T1-C3 above LOCATION column.

FIG. 3

|  | USER STATE | DATE/TIME | LOCATION |
|---|---|---|---|
|  |  | T2-C2 | T2-C3 |
| T2-R1 | HAPPY | 2011-02-24 7:05 | HOME |
| T2-R2 | HAPPY | 2011-02-24 8:34 | GYM |
| T2-R3 | HAPPY | 2011-02024 12:34 | OFFICE |
|  | HAPPY | 2011-02-25 7:12 | HOME |
|  | HAPPY | 2011-02-25 15:57 | OFFICE |
|  | SAD | 2011-02-26 7:08 | HOME |
|  | HAPPY | 2011-02-26 8:39 | GYM |
|  | HAPPY | 2011-02-26 13:44 | OFFICE |
|  | SAD | 2011-02-26 18:27 | HOME |
|  | SAD | 2011-02-27 8:30 | HOME |
|  | HAPPY | 2011-02-27 10:00 | GYM |
|  | HAPPY | 2011-02-27 18:00 | HOME |

FIG. 4

|  | USER STATE | POLLEN COUNT | DELTA (MIN) SINCE EXERCISE |
|---|---|---|---|
| T3-R1 | HAPPY | 10 | 2900 |
| T3-R2 | HAPPY | 10 | 0 |
| T3-R3 | HAPPY | 15 | 240 |
|  | HAPPY | 70 | 1358 |
|  | HAPPY | 50 | 1883 |
|  | SAD | 150 | 2794 |
|  | HAPPY | 150 | 0 |
|  | HAPPY | 40 | 305 |
|  | SAD | 150 | 588 |
|  | SAD | 100 | 1431 |
|  | HAPPY | 100 | 0 |
|  | HAPPY | 100 | 540 |

Columns: T3-C1, T3-C2, T3-C3

METHOD AND APPARATUS FOR A PREDICTIVE TRACKING DEVICE

CROSS-REFERENCE TO RELATED APPLICATION

This application is a Continuation of U.S. patent application Ser. No. 13/196,033 filed on Aug. 2, 2011.

TECHNICAL FIELD

The invention relates generally to methods and apparatus for tracking a user's mood and health symptoms.

BACKGROUND

This section introduces aspects that may be helpful in facilitating a better understanding of the inventions. Accordingly, the statements of this section are to be read in this light and are not to be understood as admissions about what is in the prior art or what is not in the prior art.

There are numerous techniques allowing a user to record journal entries regarding their mood and health symptoms.

SUMMARY

Various embodiments provide a predictive tracking method and apparatus via utilizing objective and subjective data in order to predict user states. For example, some such embodiments may allow a user to track their mood or health symptoms in relation to objective data regarding their environment in order to reveal patterns that can help forecast and proactively manage a user's mood or health symptoms.

In one embodiment, a method is provided for determining a predicted user's state near the future time. The method includes: collecting a first training set of values of a user state for a first sequence of times and a second training set of values of an environmental state for a temporally overlapping second sequence of times; retrieving, by the processor in cooperation with the digital data storage, at least one forecasted value of the environmental state at a future time; and determining, by the processor in cooperation with the digital data storage, a value of the user state near the future time based on the retrieved value of the environmental state at the future time and the collected first and second training sets.

In some embodiments, the determining is based on an association between the values of the two training sets. In a further embodiment, the determining includes associating at least one of the collected values of user state with one or more of the collected values of environmental state based on a correlation between an entry time and an identified user location of the collected value of user state and a time and a location of the one or more collected values of environmental state.

In some embodiments, the method further includes reporting a user report, the user report comprising the value of the user state near the future time. In a further embodiment, the user report further includes at least one of: an alert indicating a predicted adverse value of user state; and a remediation recommendation based on the at least one forecasted value of the environmental state at a future time.

In some embodiments, the method further includes: retrieving at least one tracking parameter; retrieving, by the processor in cooperation with the digital data storage, at least some of the second training set of values based on the at least one tracking parameter; and receiving at least some of the first training set of values from a user interface. In a further embodiment, the at least one tracking parameter specifies a triggering event that triggers an automated collection of environmental conditions.

In some embodiments, the retrieving of at least one of the values in the first training set of values includes translating a gesture on a touch screen.

In some embodiments, the retrieving of at least one of the values in the first training set of values includes analyzing a voice input to determine a user state.

In some embodiments, the retrieving of at least one of the values in the first training set of values includes receiving an indicator from a mood sensor.

In some embodiments, the retrieving at least one forecasted value of the environmental state at a future time includes: determining a future point in time and an identified location based on a calendar entry; and retrieving the at least one forecasted value of the environmental state at a future time based on the future point in time and the identified location.

In another embodiment, an apparatus is provided for determining a predicted user's state near the future time. The apparatus includes: a processor and a digital data storage connected thereto, the processor and digital data storage configured to: collect a first training set of values of a user state (occurring over) for a first sequence of times and a second training set of values of an environmental state for a temporally overlapping second sequence of times; retrieve at least one forecasted value of the environmental state at a future time; and determine a value of the user state near the future time based on the retrieved value of the environmental state at the future time and the collected first and second training sets.

In some embodiments, the apparatus further includes: a user interface configured to receive at least some of the first training set of values; and the processor and digital data storage being further configured to: retrieve at least one tracking parameter; and retrieve at least some of the second training set of values based on the at least one tracking parameter.

In some embodiments, the user interface includes a mood sensor.

In some embodiments, the digital data storage includes a calendar.

BRIEF DESCRIPTION OF THE DRAWINGS

Various embodiments are illustrated in the accompanying drawings, in which.

To facilitate understanding, identical reference numerals have been used to designate elements having substantially the same or similar structure and/or substantially the same or similar function.

DETAILED DESCRIPTION OF ILLUSTRATIVE EMBODIMENTS

Figure 1:
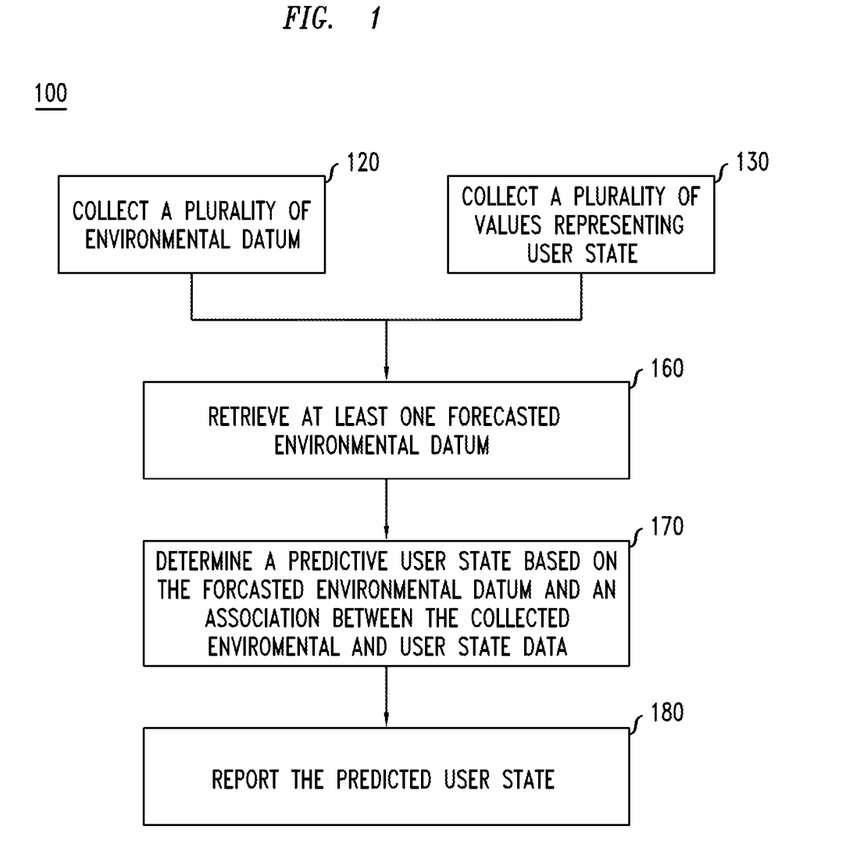
FIG. 1 depicts a flow chart illustrating an embodiment of a method for providing predictive tracking.

FIG. 1 shows a method 100 for predicting a user's state at a future time based on collected environmental and user state data. Herein, a user's state is the user's perceived emotional or physical state, e.g., the states of being happy or sad.

In the method 100, step 120 includes collecting sets of environmental conditions and times corresponding to the sets. Each set provides the environmental condition at the corresponding time. Each environmental condition is objective external information at the corresponding time that may influence a user's state. The individual sets may include value(s) of one or more environmental conditions. The step 120 may collect the environmental data from remote or local data sources or detection devices.

In the method 100, step 130 includes collecting values of the user state and times corresponding to the values. Each value provides is the user state at the corresponding time. The values of the user state are entered by the user based on the user's perception of his or her emotional or physical state.

In the method 100, step 160 includes retrieving a set of forecasted environmental conditions for a future time. The retrieved set corresponds to a future environmental condition to which the user will be subjected to at the future time.

In the method 100, step 170 includes determining a predicted user state at the future time of the step 160. In particular, step 170 includes using the set of forecasted environmental conditions retrieved in step 160 to predict the user's state at the future time based on an association between the sets of environmental conditions collected in step 120 and values of the user states collected in step 130.

In the method 100, step 180 includes reporting the predicted user state determined in step 170 to the user. The reporting involves alerting the user of his or her predicted user state.

To further illustrate the method 100 of FIG. 1, FIGS. 2-6 illustrate an example embodiment of the method 100.

Figure 2:
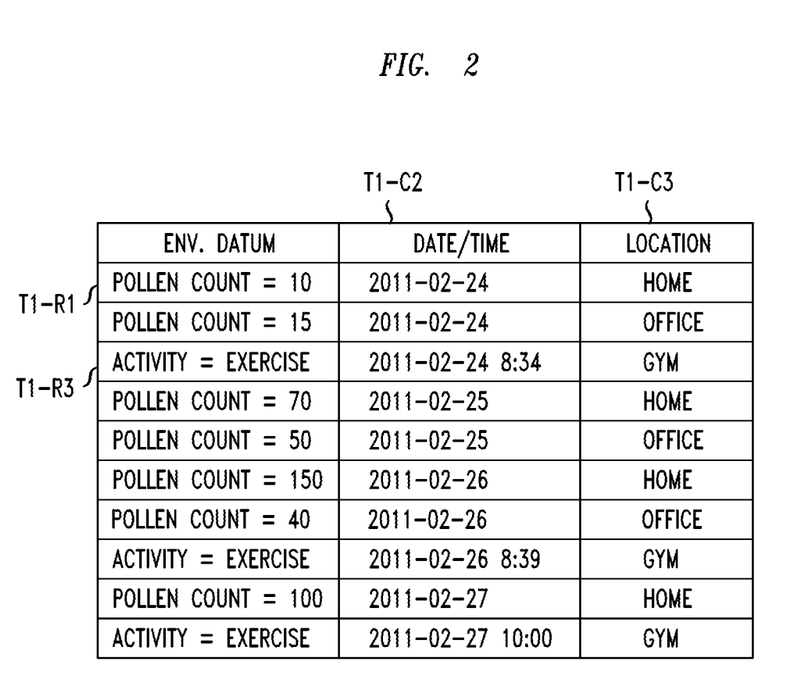
FIG. 2 illustrates an example table of collected user states.

FIG. 2 illustrates an example of sets of environmental conditions collected in step 120 of FIG. 1. The types of environmental conditions collected include pollen counts for specified dates and locations and the activity of the user. The example step 120 also collects attendant information, which includes the date/time and location corresponding to the environmental condition as illustrated in columns T1-C2 and T1-C3 respectively in FIG. 2. The sets of the environmental conditions may be received from a user by the collector of the data or may be received via an automated collection system.

Figure 3:
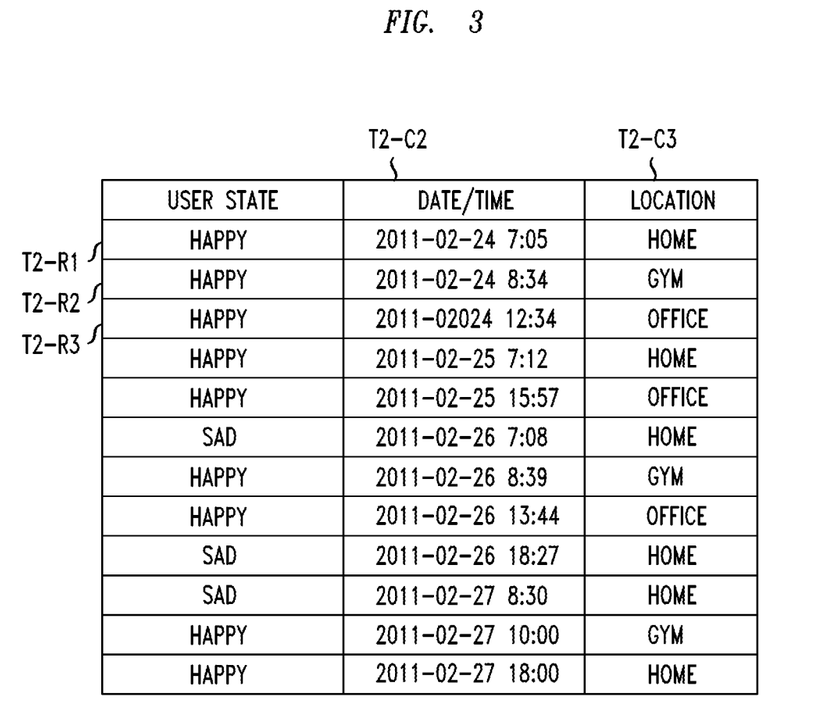
FIG. 3 illustrates an example table of collected environmental datum.

FIG. 3 illustrates example values of the user state collected in step 130 of FIG. 1. The user state has two possible values, i.e., happy and sad. The step 130 also collects attendant information, which includes the date/time and location of the user when the corresponding value of the user state was collected as illustrated in columns T2-C2 and T2-C3 respectively in FIG. 3.

It may be appreciated that the collected data shown in FIGS. 2 and 3 are illustrative. In other embodiments, larger training sets and/or more types of environmental conditions may be collected in order to improve the classification accuracy of the method.

Figure 4:
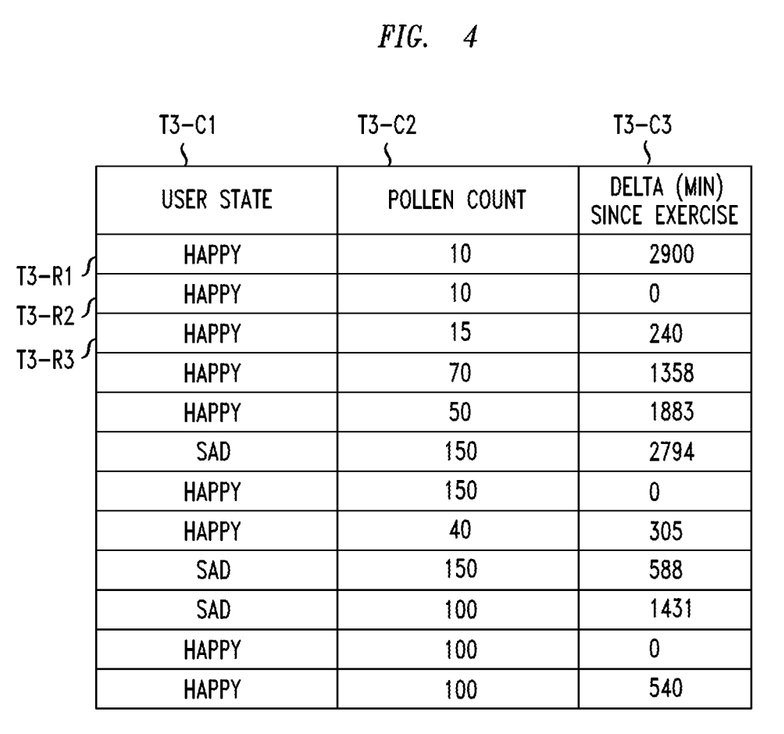
FIG. 4 illustrates an example table of associated data using the tables of FIG. 2 and FIG. 3.

FIG. 4 illustrates an example of how the collected values of the user state in FIG. 3 and the collected sets of environmental conditions in FIG. 2 may be associated in some embodiments of the method 100 at step 170. In particular, the method includes making a table in which at least a portion of the user state records of FIG. 3 are associated with one or more environmental condition records of FIG. 2.

To explain the association, each user state record is associated with one environmental condition record providing a pollen count and one environmental condition record providing a user activity value. The pollen count record corresponds with a user state record when the location from the environmental condition record is the same as the location of the user state record and the date/time from the environmental condition record is within the same calendar day as the date/time from the user state record. The user activity value record corresponds with a user state record when the date/time from the environmental condition record is the closest prior date/time of activity value records to that of the date/time of the user state record.

In other embodiments, user state records may be associated with pollen count entries of the environmental condition records when pollen counts are received for locations within a given radius or a nearest neighbor correspondence may use the pollen count for the nearest location offering pollen count data.

It may be appreciated that date/time and location correspondences between values of the user state and sets of environmental conditions may correspond exactly, may allow for ranges of correspondence or may correspond temporal and/or locational nearest neighbor sets and values. Such nearest neighbor correspondences can account for the "memory affect" of activities such as exercising and taking medication. Such nearest neighbor correspondences can account for "best" available set of environmental conditions for the location of the user, e.g., nearest location offering a set of environmental conditions.

In FIG. 4, the table includes a sequence of row entries. Each row entry corresponds to one record from the user state table in FIG. 3 and includes values derived from the associated environmental condition records from FIG. 2. The derived values indicate the expected influence that the associated set of environmental conditions has on the user state at the time the user state was collected. Column T3-C1 contains the value of the user state from the corresponding row in FIG. 3. For example, the values of user state from rows T2-R1, T2-R2 and T2-R3 from FIG. 3 are respectively contained in rows T3-R1, T3-R2 and T3-R3 in FIG. 4. Columns T3-C2 and T3-C3 contain the derived influence value of the associated sets of environmental conditions from FIG. 2.

The derived influence values in T3-C2 are simply the pollen count data extracted from the associated environmental condition record. For example, since user state data in record T2-R1 of FIG. 3 and pollen count environmental data in record T1-R1 of FIG. 2 are associated in record T3-R1, the value of the pollen count from record T1-R1 is copied into column T3-C2 of record T3-R1.

In other embodiments, the derived influence value of the pollen count may be estimated from pollen count measurements from two environmental condition records with date/times occurring prior and after the date/time of the collected user state. In some other embodiments where the pollen count for the location of the user is not available, the derived influence value of the pollen count may be estimated from pollen count measurements from two environmental condition records from neighboring locations.

The derived influence values in T3-C3 are the time intervals between the exercise activity and the collection of the user state value. Such time intervals may be derived influence values, because exercise activity may influence a user's state for a period of time after the activity. For example, since user state record T2-R2 of FIG. 3 and environmental condition record T1-R3 of FIG. 2 are associated in record T3-R2 of FIG. 4, the delta time interval between T2-R2 and T1-R3 is entered into column T3-C3 of record T3-R2. Similarly, since user state record T2-R3 of FIG. 3 and environmental condition record T1-R3 of FIG. 2 are associated in record T3-R3 of FIG. 4, the delta time interval between T2-R3 and T1-R3 is entered into column T3-C3 of record T3-R3.

Figure 5:
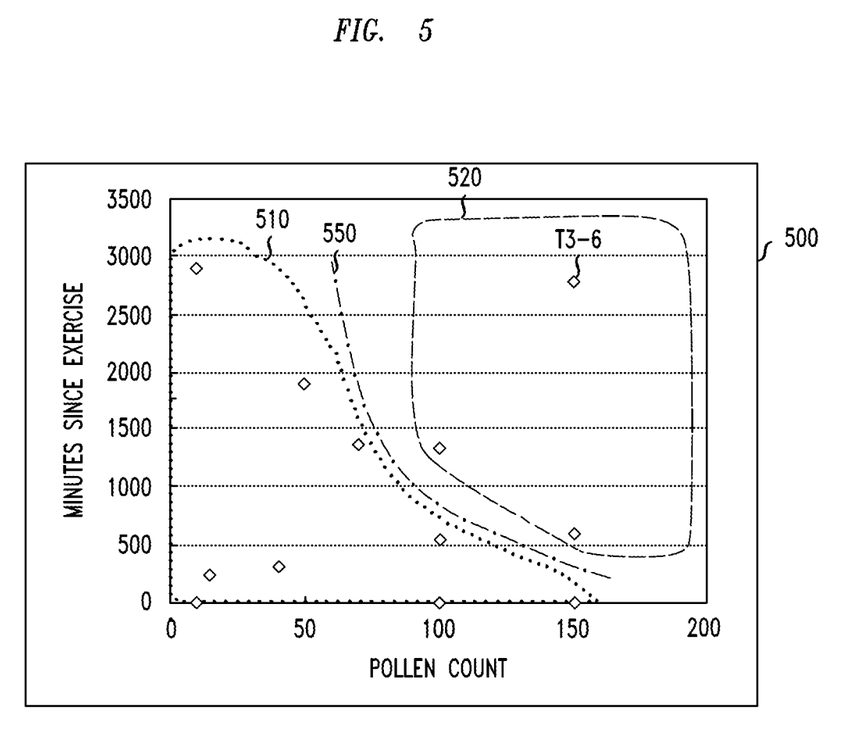
FIG. 5 illustrates an example predictive relationship plot using the data from FIG. 4.

FIG. 5 illustrates an example of how a predicted user state value may be determined from the collected data in some embodiments of the method 100 at step 170 of FIG. 1. FIG. 5 illustrates a two dimensional plot of the influence values of FIG. 4. In FIG. 5, the pollen count influence value is along the x-axis and the time "Delta" from the user's last exercise activity influence value is along the y-axis. In FIG. 4, region 510 represents those data points where the user state is "happy", and region 520 represents those data points where the user state is "sad". For example, data point T3-6 in FIG. 4 has a pollen count of 150, a time Delta of 2794 minutes and a user state of sad.

Some embodiments of the method 100 may use the data of the table of FIG. 4 to identify a "user state" classification boundary line 550 separating regions 510 and 520. The classification boundary line 550 classifies environmental data into the two user states, i.e., happy and sad, based on the side of the classification boundary line 550 at which the data point lies. Such an embodiment of the method 100 may determine the boundary based on a predictive model created by a predictive analytics program when the associated data from FIG. 4 is used as an input training set for the predictive analytics program. The classification boundary line 550 demonstrates that both pollen count and the time "Delta" from the user's last exercise activity may influence a user's state. The determined boundary may be used to subsequently predict the user's state at a future time from forecasted environmental conditions. Specifically, influence values may be derived from the forecasted environmental conditions and then used as inputs into the predictive model. The output of the predictive model is a classification of the influence values into one of the two user states.

Figure 6:
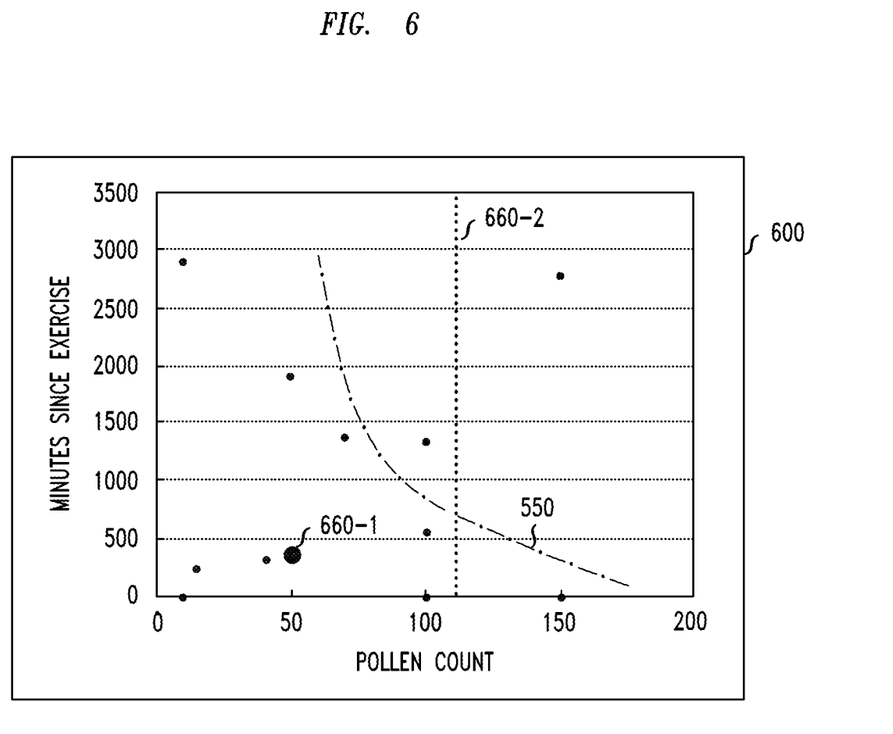
FIG. 6 illustrates an example predictive relationship plot using the data from FIG. 4.

FIG. 6 illustrates two examples of how the method 100 at step 170 may utilize the forecasted environmental conditions retrieved at step 160 to predict a future value of the user state based on the user state/environmental condition associations.

In a first retrieval example, step 160 of the method 100 retrieves forecasted environmental conditions including a pollen count of 50 for Feb. 28, 2011 and an exercise activity scheduled for 6:00 AM on Feb. 28, 2011. Based on the forecasted pollen count, the pollen count influence value is 50. Similarly, based on the difference in time between the exercise activity (i.e., 6:00 AM) and the future date/time of the predicted user's state (i.e., 12:00 PM), the value of the time "Delta" from the user's last exercise activity influence value is 360. Thus, the forecasted influence values results in data point 660-1 in FIG. 6. Since the classification boundary line 550 classifies data point 660-1 as belonging to the region where the value of user state is "happy", the method 100 predicts that the user will be happy at the corresponding future time in step 170.

In a second retrieval example, step 160 of the method 100 retrieves forecasted environmental conditions including a pollen count of 110 for Feb. 28, 2011. Based on the forecasted pollen count, the pollen count influence value is 110. The predicted user state line 660-2 represents the possible data points corresponding to a pollen count of 110. As illustrated in this example by the predicted line 660-2 traversing the classification boundary line 550, if the pollen count is 110, the predicted user state is also dependant on the time "Delta" from the user's last exercise activity influence value. Since the predicted value of the user state is not determinate in this scenario, the method 100 may report that the user's state will be dependent on the time "Delta" from the user's last exercise activity.

In some embodiments, step 170 iteratively varies the unknown "time "Delta" from the user's last exercise activity" influence value to determine when the predicted user state transitions across the classification boundary line 550 from the "sad" region to the "happy" region of FIG. 6. In this embodiment, the method 100 may report this transition value to the user.

Finally, step 180 of the method 100 reports the predicted user state to the user. The report may include any suitable information relevant to the predicted user state and its association with environmental conditions, such as: (1) the value of the predicted user state; (2) the forecasted environmental conditions; (3) alerts highlighting the environmental conditions with the highest influence; and/or (4) suggested remediation information, e.g., "Forecasted pollen count is high for tomorrow; exercise is suggested".

Referring back to FIG. 1, values of user state may be any suitable subjective indicator of a user's perception of their mood or health condition. In some embodiments of the method 100, values of user states may include: happy, angry, sad, tired, depressed, pain, congestion, fatigue, mental clarity, and/or the like.

Environmental conditions may be any suitable objective information that may influence a user's state. In some embodiments of the method 100, environmental conditions may include: a location; a user activity; a measure of pollutants or irritants (e.g., pollen count; noise level; smog level); a barometric pressure reading; a temperature; a sun index; a calendar entry; an event; a social contact (e.g., social contact with a boss may tend to introduce stress while social interaction with a wife may tend to alleviate stress) and/or the like.

In some embodiments of the method 100, a communication session parameter may be used to determine a social contact or a user activity. Communication session parameters may include: a telephone number; an email address; a text message sender/recipient; and/or communication content. In some embodiments, communication content may be parsed to determine the user activity (e.g., content may be classified as work related or leisure related). In some embodiments, a voice recognition program may be used to analyze voice communication content to identity a social contact.

In some embodiments of the method 100, step 120 further includes retrieving the collected environmental conditions. Retrieval methods may include retrieving stored environmental conditions from local digital data storage or by querying a remote data source (e.g., via a URL, RSS feed, proprietary protocol and/or the like).

In some embodiments of the method 100, step 130 further includes retrieving the values of user state. Retrieval methods may include receiving the user state values from a user interface or over a data interface. For example, an application in the cloud may receive the user input generated on a local device (e.g., a mobile phone) over the data interface.

In some embodiments of the method 100, steps 120 and/or 130 may include collecting the environmental conditions and/or values of user state using a bulk retrieval method to collect an entire set of previously stored data from another location.

In some embodiments of the method 100, steps 120 and/or 130 may include collecting the environmental conditions and/or the values of user state in a digital storage device remote from the user, e.g., in a networked cloud application.

In some embodiments of the method 100, step 130 may include allowing the user to be discrete in their data entry in order to avoid attracting attention. In some of these embodiments, step 130 may be configured to recognize special gestures upon a touch screen allowing the user to discretely record values of user state. For example, a user may draw a very simple "emoticon" (e.g., a concave curve for "happy", a convex curve for "sad", a straight line for "neutral", a circle for "scared" and a "V" for "mad") on the touch screen. Likewise, the user may use gestures to record the times when they take medication (e.g., three taps of the finger). In some further embodiments, the gestures may be defined so as to minimize detecting inadvertent user inputs. It may be appreciated that the gestures may be pre-configured or custom defined by the user.

In some embodiments of the method 100, step 160 further includes retrieving the forecasted environmental conditions from a remote source over a data interface. For example, the method 100 may include retrieving weather data or pollen count data from a content server on the internet.

In some embodiments of the method 100, step 160 further includes retrieving forecasted environmental conditions or location information for the future time from a local or remote calendar associated with the user. Retrieved forecasted environmental conditions may be scheduled activities and/or social interactions. Retrieved location information may relate to where the user will be located at the future time to facilitate retrieving forecasted environmental conditions that are location dependent.

In some embodiments of the method 100, step 160 further includes forecasting activities based on a predictive analysis of the user's history.

In some embodiments of the method 100, step 160 further includes basing the future time on a calendar entry. For example, the method may predict the value of a user state for a future time when the user has scheduled a business presentation or a social date.

In some embodiments of the method 100, step 170 may further include determining a predicted user state using a known predictive analytic technique such as: linear classifiers; Support Vector Machines; Quadratic classifiers; Kernel estimation; Boosting; Decision trees; Neural networks; Bayesian networks; Hidden Markov models and/or the like.

In some embodiments of the method 100, step 170 may further include using user profile information such as age, weight, gender and/or medical history to associate a user's profile with relevant pier groups. Advantageously, such user profile information may be associated with a pier group having associated environmental condition/user state value data sets. The associated environmental condition/user state value data sets may then be used to supplement smaller collections of user specific environmental conditions and user state values to provide more accurate classifications of predicted user state.

In some embodiments of the method 100, step 180 may further include reporting remediation information. Advantageously, remediation information provides the user with an understanding of the potential environmental conditions that may influence the predicted user state and may provide the user with suggestions to counteract an adverse predicted user state. In a first example, the forecasted environmental data may be a high pollen count which the method 100 determines may be remedied by taking identified allergy medicine or exercising. In a second example, the forecasted environmental datum may be a telephonic meeting with the user's supervisor which the method 100 determines may be remedied by either talking to another identified individual before the meeting or by scheduling the meeting to be in person or in a location with low noise levels.

In some embodiments of the method 100, step 180 may further include formatting the report in an email message; a text message; an audio message; a message displayed on a predictive tracking device and/or the like.

Figure 7:
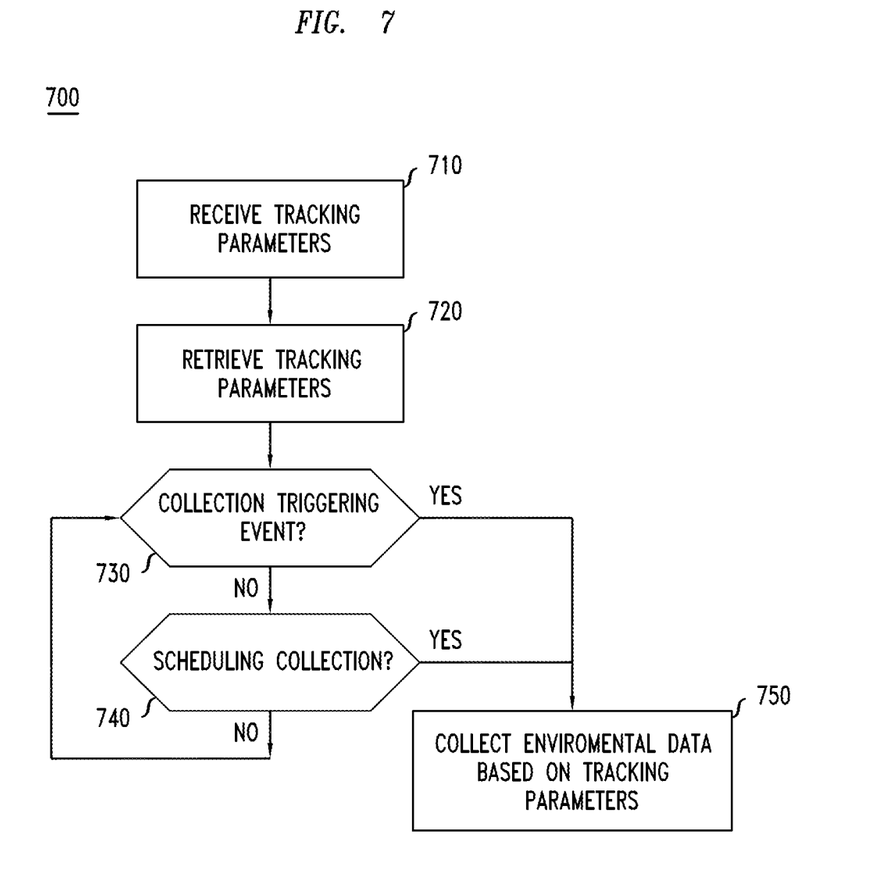
FIG. 7 depicts a flow chart illustrating a further embodiment of FIG. 1 of a method for providing predictive tracking.

FIG. 7 shows a method 700 for collecting environmental conditions which is a further embodiment of step 120 of FIG. 1. The method 700 includes receiving tracking parameters (step 710), retrieving the tracking parameters (step 720), and collecting environmental conditions based on the tracking parameters (step 750) in response to a collection being triggered by a collection event (step 730) or a scheduled automated collection (step 740).

In the method 700, step 710 includes receiving tracking parameters from a system or user. The tracking parameters specify the environmental conditions to be retrieved and how and when to retrieve those environmental conditions. The tracking parameters may identify data sources and/or communication techniques specifying how to retrieve the specified environmental conditions. The tracking parameters may also be used to configure method 700 to collect environmental conditions when a triggering event occurs and/or during scheduled date/times.

In the method 700, step 720 includes retrieving the configured tracking parameters stored in step 710 from digital data storage. The retrieved tracking parameters are used to configure the method to perform the environmental conditions collection tasks. Environmental conditions collection tasks may be performed on a per user basis and/or using a bulk retrieval method to retrieve environmental conditions that may be relevant to a group of users.

In the method 700, step 730 includes determining whether a collection triggering event specified by the tracking parameters retrieved in step 720 has been detected. The triggering event may be any suitable event that triggers an automated collection of environmental conditions such as: detection of a user's input of a value for their user state or detection that the user has moved to a new location. If a triggering event has been detected at step 730, the method proceeds to step 750, else the method proceeds to step 740.

In the method 700, step 740 includes determining whether a scheduled collection as specified by the tracking parameters retrieved in step 720 has been detected. Such a scheduled collection may be based on any suitable scheduling mechanism. For example, the scheduled collection may be based on a variety of conventional scheduling mechanisms. For example, a first scheduling mechanism may involve scheduling recurring retrievals based on a calendar time and optionally day of the week. Similarly, a second scheduling mechanism may involve scheduling recurring retrievals based on a period of time such as, "every hour". If a scheduled detection has been detected at step 740, the method proceeds to step 750, else the method returns to step 730.

It may be appreciated that the method 700 may contain step 730 and/or 740 and that the method 700 does not require both steps. It may be further appreciated that steps 730 and 740 may be performed in any order or performed in parallel.

In the method 700, step 750 includes collecting the environmental conditions based on the tracking parameters retrieved in step 720 as already described herein.

After step 740 and 750, method 700 returns to step 730 to repeat the process of collecting environmental conditions. It may be appreciated that in some embodiments, method 700 may return to either step 710 or 720 to receive updated tracking configuration parameters (step 710) or to retrieve updated tracking configuration parameters (step 720).

In some embodiments of the method 700, step 710 further includes receiving at least a portion of the tracking parameters: (1) from a user over a user interface such as a web form or a mobile applet; (2) from a user's local or remote profile information (e.g., medical records identifying that a user is allergic to ragweed pollen may be used to automate collection of ragweed pollen count information); (3) from a default collection policy stored in digital data storage; (4) from a program using learned behavior to selectively target influential environmental conditions; (5) from a system collecting bulk information which may be relevant to a group of users; and/or (6) the like.

In some embodiments of the method 700, the tracking configuration parameters include access protocol information such as FTP (File Transfer Protocol) or HTTP (Hypertext Transfer Protocol) URLs specifying how to obtain environmental conditions. In a further embodiment, step 750 further includes modifying the access protocol information based on tracking parameters, location and/or date/time. For example, a customizable URL specified in step 720 directed to a content server providing pollen count information may be modified in step 750. The modification may be to retrieve a specified type of pollen for a determined location at a specific time as illustrated in the URL below:

http://www.pollen.com/
count.asp?zip=07074&type=ragweed&datetime=now.

In these embodiments, step 750 may further include parsing the returned information to extract the environmental conditions. In a further embodiment, the returned information may be in a formatted language such as XML to facilitate parsing the returned information.

In some embodiments of the method 700, step 750 further includes retrieving sets of environmental conditions: (1) in bulk prior to or after a user's input of user state values; (2) from a central location storing environmental conditions for a number of users; and/or (3) by storing user inputs for a period of time and then downloading a batch of associated environmental conditions at a later time. For example, if a user's device does not have a wireless connection or is outside of a service area with data connectivity, the associated environmental conditions may be downloaded at a later time using a wired connection or when wireless data communication becomes available.

In some embodiments of the method 700, step 750 further includes receiving a location identifier representing the location of the user from a GPS device local to the user. The location identifier may be used in step 750 to retrieve environmental conditions based on the location identifier. In some embodiments, the method may receive the identified location information directly from the GPS. In other embodiments, the method may receive the identified location information over a data interface from a remote device, for example, when the method is being performed remote from the user (e.g., cloud computing).

Although primarily depicted and described in a particular sequence, it may be appreciated that the steps shown in methods 100 and 700 may be performed in any suitable sequence. Moreover, the steps identified by one box may also be performed in more than one place in the sequence.

It may be appreciated that steps of various above-described methods can be performed by programmed computers. Herein, some embodiments are also intended to cover program storage devices, e.g., digital data storage media, which are machine or computer readable and encode machine-executable or computer-executable programs of instructions, wherein said instructions perform some or all of the steps of said above-described methods. The program storage devices may be, e.g., digital memories, magnetic storage media such as a magnetic disks and magnetic tapes, hard drives, or optically readable digital data storage media. The embodiments are also intended to cover computers programmed to perform said steps of the above-described methods.

Figure 8:
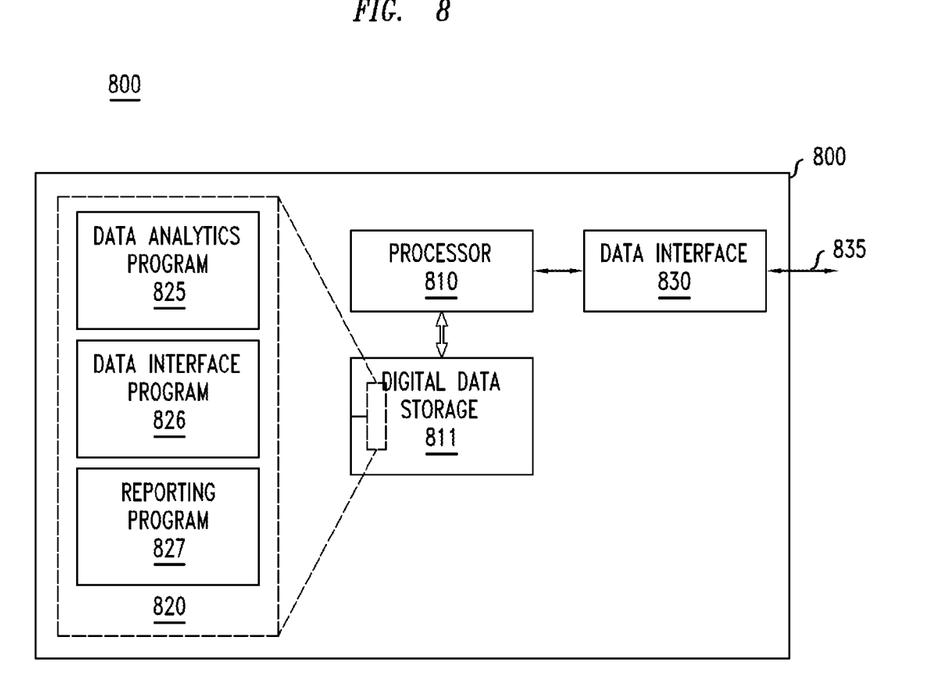
FIG. 8 depicts a block diagram schematically illustrating one embodiment of a predictive tracking device.

FIG. 8 schematically illustrates one embodiment of a predictive tracking device 800 for predicting a user's state at a future time based on collected environmental and user state data, e.g., using the methods 100 and/or 700. The predictive tracking device 800 includes a processor 810, a digital data storage 811 and a data interface 830.

The processor 810 controls the operation of predictive tracking device 800. The processor 810 cooperates with the digital data storage 811 and data interface 830.

The digital data storage 811 stores collected values of user state and environmental conditions. It may be appreciated that values of user state and environmental conditions may be stored separately or may be associated and combined into one storage location. The digital data storage 811 also stores programs 820 executable by the processor 810.

The processor-executable programs 820 may include a data analytics program 825, data interface program 826, and a reporting program 827. Processor 810 cooperates with processor-executable programs 820 to perform the steps of methods 100 and 700. For example, processor 810 may perform step 170 of method 100 by executing the data analytics program 825. Similarly, processor 810 may perform step 180 of method 100 by executing the reporting program 827. Additionally, processor 810 cooperates with digital processor-executable programs 820 to control the predictive tracking device. For example, processor 810 may execute the data interface program 826 to control data interface 830.

The data interface 830 is configured to retrieve or transmit data between predictive tracking device 800 and external data sources and destinations via communication channel 835. Communication channel 835 may be any conventional communication path/communication protocol supporting data connectivity. Although depicted and described as a single communication channel 835, data interface 830 may be configured for supporting any suitable number of communication channels supporting any suitable number(s) of sessions (e.g., any suitable number of IP flows), which may be directed between data interface 830 and/or any other suitable external source of communications via communication channel 835.

The data interface 830 may support the retrieval and transmission of data in various steps of the methods 100 and 700. For example: (1) steps 120 and 160 in method 100 and step 750 in method 700 may receive sets of environmental conditions from an internet web site or a data server; (2) step 130 in method 100 may receive values of user state from a remote user input device; (3) step 180 in method 100 may transmit reports in the form of emails or text messages; (3) step 710 in method 700 may receive tracking parameters from an external source; and/or (4) step 720 in method 700 may retrieve tracking parameters from an external source.

In some embodiments, the data interface 830 may support retrieving or transmitting data over one or more of the following communication channels 835: wireless communications (e.g., GSM, CDMA, bluetooth); wire line communications; packet network communications (e.g., IP); VoIP communications (e.g., SIP); broadband communications (e.g., DOCSIS and DSL); and the like.

Figure 9:
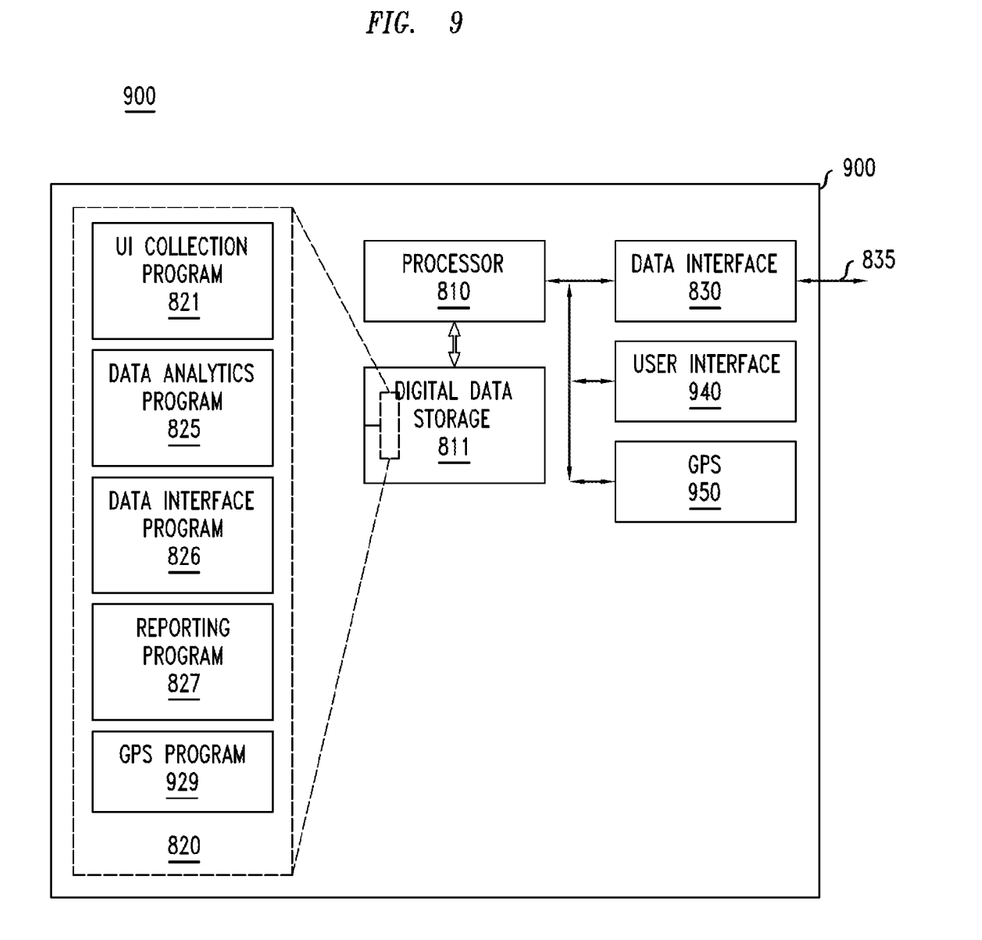
FIG. 9 depicts a block diagram schematically illustrating a further embodiment of the predictive tracking device of FIG. 7.

FIG. 9 schematically illustrates a further embodiment 900 of the predictive tracking device 800 of FIG. 8. The predictive tracking device 900 further includes a user interface 940 and a GPS 950. The processor-executable programs 820 further include a UI collection program 921 and a GPS program 929 that are executable by the processor 810.

The processor 810 can execute the UI collection program 921 to collect user input from the user interface 940 and the GPS program 929 to interface with GPS 950.

The user interface 940 may be any suitable interface capable of receiving user input and/or conveying content to the user, e.g., in steps 130 and 180 in method 100. The user interface 940 may include: a keypad; a display; a touch screen; buttons/switches; a microphone, a speaker; a speech recognition interface; a motion sensor; a mood sensor and/or the like.

The GPS 950 may be a conventional GPS device used to retrieve a location identifier representing the location of predictive tracking device 900. The location identifier may be used in steps 120 and/or 160 in method 100 and/or step 750 in method 700 to retrieve environmental conditions based on the location identifier.

In some embodiments, the user interface 940 may be a microphone. In some of these embodiments, the microphone may be used to determine noise in the user's surrounding environment to collect environmental conditions related to noise levels, e.g., in step 120 in method 100 and/or step 750 in method 700. Measurement of any suitable characteristic of noise may be collected. For example, measurements may include: level; frequency, intermittency, and/or periodicity.

In some of the embodiments having a microphone as a user interface 940, the microphone may capture a user's voice input. The predictive tracking device 900 may advantageously automatically detect and collect a user's state by analyzing the received voice using conventional voice detection methods, e.g., in step 130 in method 100. For example, a voice analysis program may measure fundamental frequency (FO), jitter, shimmer, and/or Harmonic Noise Ratio (HNR) and compare the values to known values characterizing a user's mood based on these measured values to determine a user's state.

In some embodiments, the user interface 940 may be a mood sensor. The mood sensor may automatically detect and collect values of a user's state, e.g., in step 130 in method 100. The mood sensor may determine the values of a user's state by measuring changes in skin temperature, motion, and/or skin conductivity.

In some embodiments of the predictive tracking device 900, the values of a user's state may automatically be collected, e.g., in step 130 in method 100. Vlues of the user state may be automatically collected: (1) in response the interface detecting the value of a user's state detects an abrupt change in the value of a user state; (2) during predetermined intervals; and/or (3) whenever a change of of a value of the user's state occurs.

In some embodiments of the predictive tracking device 900, the tracking program may run in the background so as to enable the user to enter input from any operating state of his/her predictive tracking device. For example, the user may be enabled to enter such input while in a telephony call without opening a designated predictive tracking application. In some embodiments, the predictive tracking device 900 may allow annotating the user input, e.g., a value of the user's state. For example, the user may annotate entries of user input by: selecting an option from a menu displayed on the touch screen; entering text on the key pad; adding a spoken comment; and/or the like.

In some embodiments, predictive tracking device 800 and/or 900 is a machine-executable program of instructions executing on a mobile computing device. A mobile computing device may be any suitable mobile device such as: a mobile phone, a tablet, a computer, a personal digital assistant (PDA), an e-reader and the like.

In some embodiments, predictive tracking device 800 and/or 900 is a machine-executable program of instructions executing on a networked host. A networked host may be any suitable host such as: a single server and multiple servers in a cloud computing network. In a further embodiment, the user input device may be a mobile computing device.

Although depicted and described herein with respect to embodiments in which, for example, programs and logic are stored within the digital data storage and the memory is communicatively connected to the processor, it may be appreciated that such information may be stored in any other suitable manner (e.g., using any suitable number of memories, storages or databases); using any suitable arrangement of memories, storages or databases communicatively coupled to any suitable arrangement of devices; storing information in any suitable combination of memory(s), storage(s) and/or internal or external database(s); or using any suitable number of accessible external memories, storages or databases. As such, the term digital data storage referred to herein is meant to encompass all suitable combinations of memory(s), storage(s), and database(s).

The description and drawings merely illustrate the principles of the invention. It will thus be appreciated that those skilled in the art will be able to devise various arrangements that, although not explicitly described or shown herein, embody the principles of the invention and are included within the invention's spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

The functions of the various elements shown in the FIGS., including any functional blocks labeled as "processors", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included. Similarly, any switches shown in the FIGS. are conceptual only. Their function may be carried out through the operation of program logic, through dedicated logic, through the interaction of program control and dedicated logic, or even manually, the particular technique being selectable by the implementer as more specifically understood from the context.

It may be appreciated that any block diagrams herein represent conceptual views of illustrative circuitry embodying the principles of the invention. Similarly, it may be appreciated that any flow charts, flow diagrams, state transition diagrams, pseudo code, and the like represent various processes which may be substantially represented in computer readable medium and so executed by a computer or processor, whether or not such computer or processor is explicitly shown.

What is claimed is:

1. A method, comprising:
   at a processor and a digital data storage connected thereto, collecting a first training set of values of a user state for a first sequence of times and a second training set of values of an environmental state for a temporally overlapping second sequence of times;
   retrieving, by the processor in cooperation with the digital data storage, at least one forecasted value of the environmental state at a future time; and
   determining, by the processor in cooperation with the digital data storage, a value of the user state at the future time based on the retrieved value of the environmental state and the collected first and second training sets.

2. The method of claim 1, wherein the act of determining is based on an association between the values of the two training sets.

3. The method of claim 2, wherein the determining comprises:
   associating at least one of the collected values of user state with one or more of the collected values of environmental state based on a correlation between an entry time and an identified user location of the collected value of user state and a time and a location of the one or more collected values of environmental state.

4. The method of claim 1, wherein a plurality of the collected values of the environmental state includes at least one of:
   a pollutant measurement;
   a barometric pressure reading;
   a temperature reading;
   a sun index reading; and
   a calendar entry.

5. The method of claim 1, wherein a plurality of the collected values of the environmental state includes a noise measurement.

6. The method of claim 1, wherein a plurality of the collected values of the environmental state includes a communication session parameter and the communication session parameter includes at least one of:
   a telephone number;
   an email address;
   a text message recipient; and
   communication content.

7. The method of claim 1, further comprising reporting, by the processor in cooperation with the digital data storage, a user report, the user report comprising the value of the user state near the future time.

8. The method of claim 7, wherein the reporting comprises at least one of:
   sending an email;
   displaying an alert on a user interface; and
   delivering an audible to a user interface.

9. The method of claim 7, wherein the user report further comprises at least one of:
   an alert indicating a predicted adverse value of user state; and
   a remediation recommendation based on the at least one forecasted value of the environmental state at a future time.

10. The method of claim 1, further comprising:
    retrieving, by the processor in cooperation with the digital data storage, at least one tracking parameter;
    retrieving, by the processor in cooperation with the digital data storage, at least some of the second training set of values based on the at least one tracking parameter; and
    receiving at least some of the first training set of values from a user interface.

11. The method of claim 10, wherein at least one tracking parameter specifies a triggering event that triggers an automated collection of environmental conditions.

12. The method of claim 10, further comprising receiving a location identifier representing the identified location from a GPS, wherein the retrieving of at least one of the values in the second training set of values is further based on the identified location.

13. The method of claim 10, wherein the retrieving of at least one of the values in the first training set of values comprises translating a gesture on a touch screen.

14. The method of claim 10, wherein the retrieving of at least one of the values in the first training set of values comprises analyzing a voice input to determine a user state.

15. The method of claim 10, wherein the retrieving of at least one of the values in the first training set of values comprises receiving an indicator from a mood sensor.

16. The method of claim 1, wherein the retrieving at least one forecasted value of the environmental state at a future time comprises:
    determining a future point in time; and
    retrieving the at least one forecasted value of the environmental state at a future time based on the future point in time.

17. An apparatus, comprising:
    a processor and a digital data storage connected thereto, the processor and the digital data storage configured to:
    collect a first training set of values of a user state for a first sequence of times and a second training set of values of an environmental state for a temporally overlapping second sequence of times;
    retrieve at least one forecasted value of the environmental state at a future time; and
    determine a value of the user state at the future time based on the retrieved value of the environmental state and the collected first and second training sets.

18. The apparatus of claim 17, wherein the apparatus is a mobile computing device.

19. The apparatus of claim 17, wherein the apparatus is a networked host.

20. The apparatus of claim 17, further comprising:
    a user interface configured to receive at least some of the first training set of values; and
    the processor and digital data storage being further configured to:
    retrieve at least one tracking parameter; and retrieve at least some of the second training set of values based on the at least one tracking parameter.

21. The apparatus of claim 20, further comprising a GPS configured to determine an identified location of the apparatus and wherein the system is further configured to associate at least one of the collected values of user state with one or more of the collected values of environmental state based on a correlation between an entry time and the identified location of the collected value of user state and a time and a location of the one or more collected values of environmental state.

22. The apparatus of claim 20, wherein the user interface comprises a mood sensor.

23. The apparatus of claim 20, wherein the digital data storage comprises a calendar.

24. A digital data storage medium encoding a machine-executable program of instructions to perform a method, the method comprising:
at a processor and a digital data storage connected thereto, collecting a first training set of values of a user state for a first sequence of times and a second training set of values of an environmental state for a temporally overlapping second sequence of times;
retrieving, by the processor in cooperation with the digital data storage, at least one forecasted value of the environmental state at a future time; and
determining, by the processor in cooperation with the digital data storage, a value of the user state at the future time based on the retrieved value of the environmental state and the collected first and second training sets.

25. The digital data storage medium encoding a machine-executable program of instructions of claim 24, wherein the determining comprises:
associating at least one of the collected values of user state with one or more of the collected values of environmental state based on a correlation between an entry time and an identified user location of the collected value of user state and a time and a location of the one or more collected values of environmental state.

26. The digital data storage medium encoding a machine-executable program of instructions of claim 24, further comprising reporting a user report, the user report comprising at least one of:
an alert indicating a predicted adverse value of user state; and
a remediation recommendation based on the at least one forecasted value of the environmental state at a future time.

27. The digital data storage medium encoding a machine-executable program of instructions of claim 24, further comprising:
retrieving, by the processor in cooperation with the digital data storage, at least one tracking parameter;
retrieving, by the processor in cooperation with the digital data storage, at least some of the second training set of values based on the at least one tracking parameter; and
receiving at least some of the first training set of values from a user interface.

28. The digital data storage medium encoding a machine-executable program of instructions of claim 27, wherein at least one tracking parameter specifies a triggering event that triggers an automated collection of environmental conditions.

29. The apparatus of claim 17, wherein a plurality of the collected values of the environmental state includes a noise measurement.

30. The apparatus of claim 17, wherein the determination comprises:
associating at least one of the collected values of user state with one or more of the collected values of environmental state based on a correlation between an entry time and an identified user location of the collected value of user state and a time and a location of the one or more collected values of environmental state.

* * * * *